United States Patent
Smith et al.

(10) Patent No.: US 8,571,364 B2
(45) Date of Patent: Oct. 29, 2013

(54) MULTI-SPOT LASER PROBE WITH FACETED OPTICAL ELEMENT

(75) Inventors: Ronald T. Smith, Irvine, CA (US); Michael A. Zica, Costa Mesa, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 89 days.

(21) Appl. No.: 13/292,231

(22) Filed: Nov. 9, 2011

(65) Prior Publication Data

US 2013/0114927 A1 May 9, 2013

(51) Int. Cl.
*G02B 6/32* (2006.01)

(52) U.S. Cl.
USPC .................................. 385/35; 385/33; 29/428

(58) Field of Classification Search
USPC ......... 385/35, 33; 606/13; 362/553, 572, 556; 156/242
See application file for complete search history.

(56) References Cited

U.S. PATENT DOCUMENTS

| | | | |
|---|---|---|---|
| 4,695,124 A | 9/1987 | Himono et al. | |
| 5,738,676 A | 4/1998 | Hammer et al. | |
| 5,921,981 A | 7/1999 | Bahmanyar et al. | |
| 6,096,028 A * | 8/2000 | Bahmanyar et al. | 606/4 |
| 7,027,478 B2 | 4/2006 | Ackley | |
| 7,343,770 B2 | 3/2008 | Barnoski et al. | |
| 7,566,173 B2 * | 7/2009 | Auld et al. | 383/33 |
| 8,035,902 B2 | 10/2011 | Ishii et al. | |
| 2004/0091215 A1 | 5/2004 | Barnoski et al. | |
| 2009/0244727 A1 | 10/2009 | Ishii et al. | |
| 2011/0044585 A1 * | 2/2011 | Seng | 385/60 |
| 2011/0141759 A1 | 6/2011 | Smith | |
| 2011/0144627 A1 | 6/2011 | Smith | |
| 2013/0041356 A1 | 2/2013 | Smith et al. | |

* cited by examiner

*Primary Examiner* — Ellen Kim
(74) *Attorney, Agent, or Firm* — Keiko Ichiye

(57) ABSTRACT

In certain embodiments, a method includes forming a ferrule from a portion of a tube. The tube is cut to yield the ferrule and a short cannula. A multi-spot generator with a faceted optical element is added to the short cannula. An optical fiber is placed into the ferrule, and the ferrule and the short cannula are assembled. In certain embodiments, a system includes a long cannula, an optical fiber, and a multi-spot generator. The optical fiber can carry a laser beam to a distal end of the long cannula. The multi-spot generator is located at the distal end and comprises a faceted optical element and a ball lens. The faceted optical element can be formed directly onto or separately from the ball lens. The ball lens can be spherical or hemispherical.

16 Claims, 4 Drawing Sheets

MULTI-SPOT LASER PROBE WITH FACETED OPTICAL ELEMENT

TECHNICAL FIELD

The present disclosure relates generally to optical surgical probes, and more particularly to a multi-spot laser probe with a faceted optical element.

BACKGROUND

In some applications, optical surgical probes may deliver light to multiple spots at a surgical target. For example, in photocoagulation of retinal tissue, multiple spots may reduce the time of the procedure. Various techniques have been employed to produce multiple beams for a multi-spot pattern. For example, one approach uses diffractive elements at the distal end of the probe to divide an incoming beam into multiple beams.

Difficulties, however, can arise with using diffractive elements at the distal end of the probe. As one example, diffractive elements produce a multitude of higher diffraction orders. While these orders have a lower light intensity as compared to the primary spot pattern, they may still have some effect. As another example, a diffractive element may not perform the same in different refractive media. For example, a diffractive element may be placed into a medium with a different refractive index than that of air, and spaces between the diffractive elements may fill with the medium, which may affect the spot pattern. As yet another example, the spacing between the spots can vary for different wavelengths, which can cause problems if an aiming beam and a treatment beam are different colors. Lastly, diffractive elements are frequently expensive and difficult to produce, especially if the diffractive element is to fit into a small area, such as a distal tip of a surgical probe for surgical instruments that are 23-gauge or smaller.

BRIEF SUMMARY

In certain embodiments, a method includes forming a ferrule from a portion of a tube having an interior region. The tube is cut to yield the ferrule and a short cannula. A multi-spot generator is added to the interior region of the short cannula. The multi-spot generator has a faceted optical element with a faceted end surface. At least one optical fiber is placed into the interior region of the ferrule, and the ferrule and the short cannula are assembled.

In certain embodiments, a system includes a long cannula, at least one optical fiber, and a multi-spot generator. The optical fiber is disposed within the long cannula and configured to carry a laser beam from a laser source to the distal end of the long cannula. The multi-spot generator is located at the distal end of the long cannula and comprises a faceted optical element and a ball lens. The faceted optical element is formed separately from the ball lens and has a faceted end surface that includes at least one facet oblique to a path of the laser beam. The faceted optical element is configured to receive the laser beam from the optical fiber, and the ball lens is configured to receive the laser beam from the faceted optical element.

In certain embodiments, a system includes a long cannula, at least one optical fiber, and a multi-spot generator. The optical fiber is disposed within the long cannula and configured to carry a laser beam from a laser source to the distal end of the long cannula. The multi-spot generator is located at the distal end of the long cannula and comprises a faceted optical element and a hemispherical ball lens. The faceted optical element has a faceted end surface that includes at least one facet oblique to a path of the laser beam. The faceted optical element is configured to receive the laser beam from the optical fiber, and the hemispherical ball lens is configured to receive the laser beam from the faceted optical element.

BRIEF DESCRIPTION OF THE DRAWINGS

Exemplary embodiments of the present disclosure will now be described by way of example in greater detail with reference to the attached figures, in which.

DETAILED DESCRIPTION OF EXAMPLE EMBODIMENTS

Figure 1:
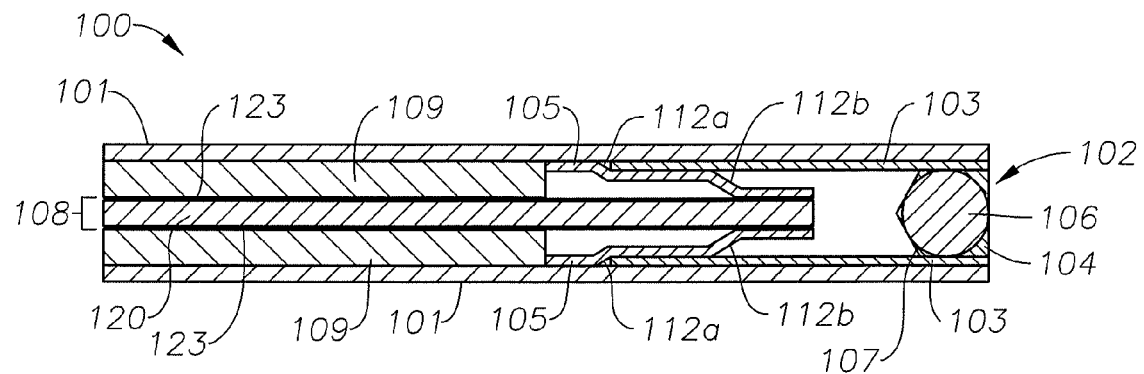
FIG. 1 illustrates an example of a distal end of a long cannula for an optical surgical probe according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of a distal end of a cannula system 100 for an optical surgical probe that includes a multi-spot generator 102 disposed within a short cannula 103 and an optical fiber 108 disposed within a ferrule 105 in accordance with certain embodiments. In certain embodiments, short cannula 103 and ferrule 105 may be formed from the same tube, which may allow for easier self-alignment of short cannula 103 and ferrule 105. Also, multi-spot generator 102 may have many different embodiments described in more detail below.

In the illustrated example, cannula system 100 includes a long cannula 101. A short cannula 103, a ferrule 105, and an inner cylinder 109 are disposed within long cannula 101. A portion of ferrule 105 is disposed within short cannula 103. An optical fiber 108 is disposed within inner cylinder 109 and ferrule 105. A multi-spot generator 102 is disposed within a short cannula 103. A multi-spot generator 102 includes a ball lens 106 and a faceted optical element 104. The faceted optical element 104 has a faceted end surface 107. "Distal" refers to a direction along cannula system 100 that is towards a target area, and "proximal" refers to the opposite direction.

Cannula system 100 may be used for a surgical instrument inserted into a human (or other living or previously living) body for medical purposes, such as for ophthalmic surgery. For example, cannula system 100 may be used as a surgical instrument for performing surgery inside of an eyeball. Cannula system 100 may be configured to optically couple to a laser source and to deliver a laser beam from the laser source to a target. In this document, a laser beam received by a first component from a second component or transmitted to a first component from a second component may go through zero, one, or more other components between the first and second components.

Long cannula 101 may be a hollow cylinder comprising any suitable material, e.g., a metal such as stainless steel. Inner cylinder 109 is disposed within a portion of long cannula 101 and may hold optical fiber 108 into place relative to multi-spot generator 102. Inner cylinder 109 may comprise any suitable material that can provide structural support for optical fiber 108. Optical fiber 108 delivers a laser beam to multi-spot generator 102 located at a distal end of cannula system 100. Optical fiber 108 may be any suitable structure for transmitting light. In the example, optical fiber 108 has a core 120 and a cladding/jacket 123. Any suitable size of optical fiber 108 may be used, e.g., core 120 may be 75 to 150 microns. A larger core 120 generally yields a larger spot. The central axis of the beam emitted from optical fiber 108 is the "beam path."

Short cannula 103 houses multi-spot generator 102, and ferrule 105 holds optical fiber 108. Both short cannula 103 and ferrule 105 may be configured to fit together to align optical fiber 108 and multi-spot generator 102. In this example, ferrule 105 has two tapers 112 (112a-b). A "taper" is a decrease in diameter.

In certain embodiments, short cannula 103 and ferrule 105 are fashioned from the same tube, which may allow for easier self-alignment of short cannula 103 and ferrule 105. "Alignment" may be defined in any suitable manner. For example, two parts are aligned if the rotational axis of one part substantially coincides with the rotational axis of the other part. As another example, two parts are aligned if substantially all of a laser beam transmitted by one part is received by the other part.

The tube may have any suitable shape and size, such as a substantially cylindrical shape that defines an interior region. The cylindrical shape may have any suitable length and diameter that can fit within long cannula 101, such as a length in the range of 25 to 50 millimeters (mm) and a diameter in the range of 1 mm or less. The tube may comprise any suitable material, e.g., a metal such as stainless steel. Formation of short cannula 103 and ferrule 105 is described in more detail below.

Multi-spot generator 102 splits a laser beam to yield a multi-spot beam, or multiple beams that can produce multiple laser spots at a target. In the example, a laser beam emitted by optical fiber 108 diverges. Faceted end surface 107, spaced apart from the distal end of optical fiber 108, refracts portions of the diverging beam to different locations to yield a multi-spot beam. Ball lens 106 transmits the multi-spot beam out of a planar distal surface of faceted optical element 104.

In the example, multi-spot generator 102 includes a faceted optical element 104 with a faceted end surface 107 disposed proximally from a ball lens 106. Faceted optical element 104 is an optical element with a faceted end surface 107. A "faceted" optical element refers to an optical element having a faceted surface. A "faceted surface" is a surface formed of multiple subsurfaces, or "facets", where the intersections between the facets are greater than or less than 180 degrees so as not to appear smooth. The facets may be, but need not be, planar, e.g., a facet may be curved. "Concave" and "convex" in this context refer to whether the faceted surface is formed inwardly or outwardly of the optical element along the beam path. In the example, faceted end surface 107 is convex and points toward optical fiber 108. A faceted end surface may provide optical focusing power.

Faceted end surface 107 may have any suitable number and shape of facets. In certain embodiments, faceted end surface 107 may have N facets oblique to the beam path that meet at a point aligned with the center of the laser beam from optical fiber 108 such that multi-spot generator 102 produces N output spots, where N=3, 4, 5, . . . . In other embodiments, faceted end surface 107 may have a central planar facet perpendicular to the beam path with N surrounding obliquely-angled facets to produce a central spot surrounded by N spots. Any suitable slant angle between the facets may be used. In general, decreasing the slant angle decreases the separation between the spots. In certain embodiments, at least one facet is oriented "oblique to the beam path" such that a direction normal to a facet at a center of the facet is not parallel to the beam path of the laser beam.

Faceted optical element 104 may be formed of an optical adhesive, which may provide technical advantages in certain embodiments. One advantage is that optical adhesives have a useful range of refractive indices. Another advantage is that forming the faceted surface from an optical adhesive is relatively easy. A third advantage is that the optical adhesive material is relatively durable compared to other optical elements. A fourth advantage is that the optical adhesive may be formed around other optical components, such as ball lens 106.

Ball lens 106 is an optical element that focuses an incident beam to collimate or converge the beam on the distal side of ball lens 106. A sapphire ball lens is an example of ball lens 106. Ball lens 106 may have any suitable shape, such as a sphere, an approximate sphere, or a portion of a sphere (e.g., a hemisphere). Ball lens 206 may comprise any refractive material for transmitting light from the laser source through the lens.

In certain embodiments, ball lens 106 and faceted optical element 104 have different refractive indices. To focus a collimated or converging beam, the refractive index of ball lens 106 should be greater than that of the adhesive medium of faceted optical element 104. For example, ball lens 106 may be a sapphire ball lens with a visible refractive index of roughly 1.76, and faceted optical element 104 may have a lower adhesive refractive index of 1.57 to 1.58.

In other embodiments, faceted end surface 107 can be concave. Ball lens 106 converges the beams to produce a multi-spot pattern. The pattern spreads relatively little as the beams move away from the end of cannula system 100. The allows the multi-spot pattern to have a more consistent spot spacing as the distance between the distal end of the cannula system 100 and the target area changes.

Depending on the relative refractive indices of faceted optical element 104 and the medium into which the surgical probe is inserted, the spots could further diverge as they pass from the distal face of faceted optical element 104 into the medium.

Figure 2:
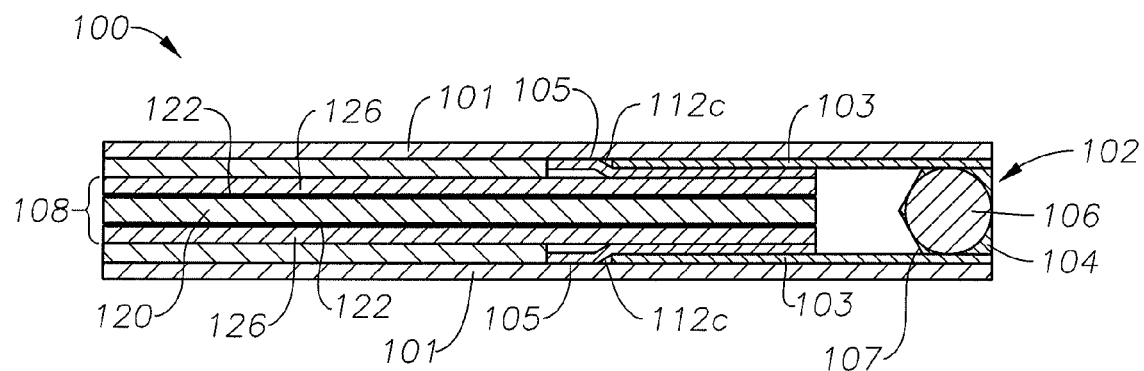
FIG. 2 illustrates another example of a distal end of a long cannula for an optical surgical probe according to certain embodiments.

FIG. 2 illustrates another example of a distal end of a cannula system 100 for an optical surgical probe that includes a ferrule 105 with one taper 112c. The inner diameter of ferrule 105 may be larger than the diameter of a typical optical fiber, such as a 75 micron core glass fiber, which has a 90 micron cladding diameter and a 101 micron buffer diameter. In the example, optical fiber 108 has a cladding 122 and a buffer layer 126 that is larger than the typical buffer layer. The outer diameter of buffer layer 126 may be approximately the same as (or slightly larger than) the inner diameter of ferrule 105. Optical fiber 108 may then be press-fit into ferrule 105.

Figure 3:
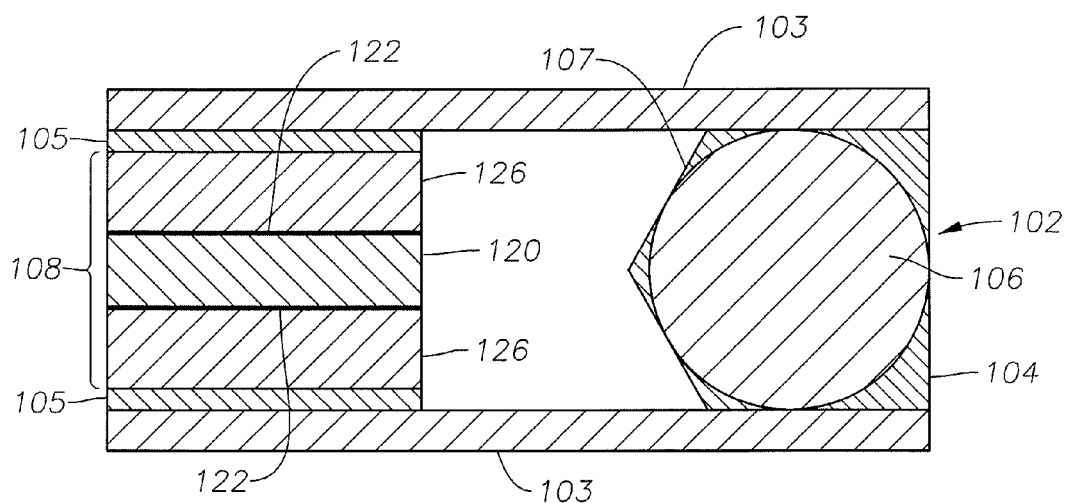
FIG. 3 illustrates an example of a multi-spot generator with a spherical ball lens according to certain embodiments.

FIG. 3 illustrates an example of a multi-spot generator 102 with a spherical ball lens 106. In the example, multi-spot generator 102 includes a faceted optical element 104 formed around a spherical ball lens 106. Multi-spot generator 102 may emit spots that are round.

Figure 4:
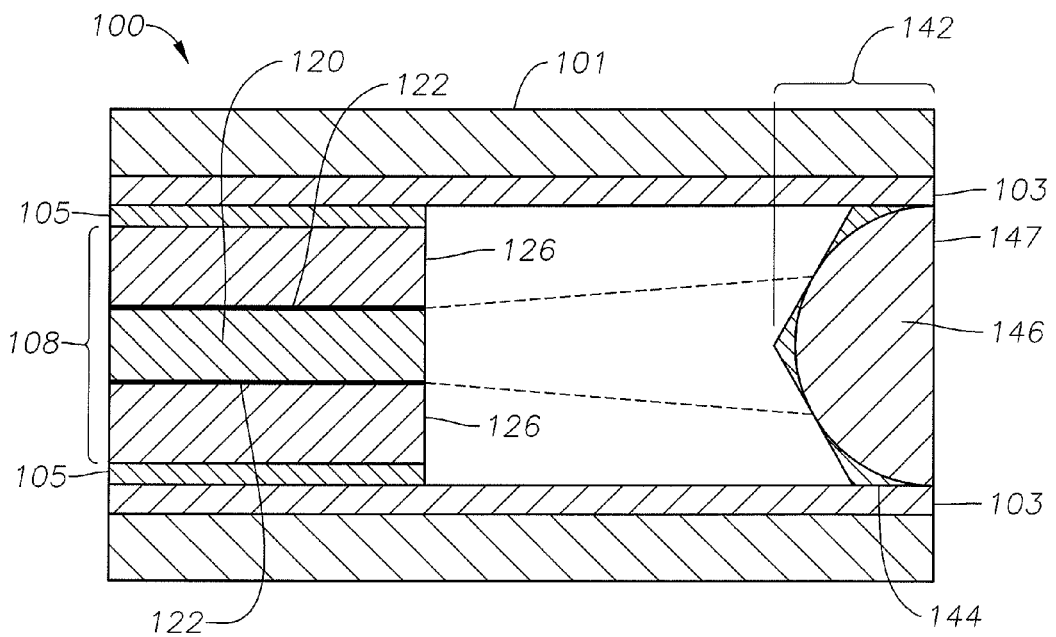
FIG. 4 illustrates an example of a multi-spot generator with a hemispherical ball lens according to certain embodiments.

FIG. 4 illustrates an example of a multi-spot generator 142 with a hemispherical ball lens 146. In the example, multi-spot generator 142 includes a faceted optical element 104 disposed in a proximal direction from a hemispherical ball lens 146 with a planar surface 147. In this example, the cured adhesive is only on the proximal side of ball lens 146, and planar surface 147 is flush with the distal end of short cannula 103 and long cannula 101. Multi-spot generator 142 may emit spots that are elliptical. If optical fiber 108 is farther away from faceted end surface 107, the resulting spots may become rounder and smaller.

Figure 5:
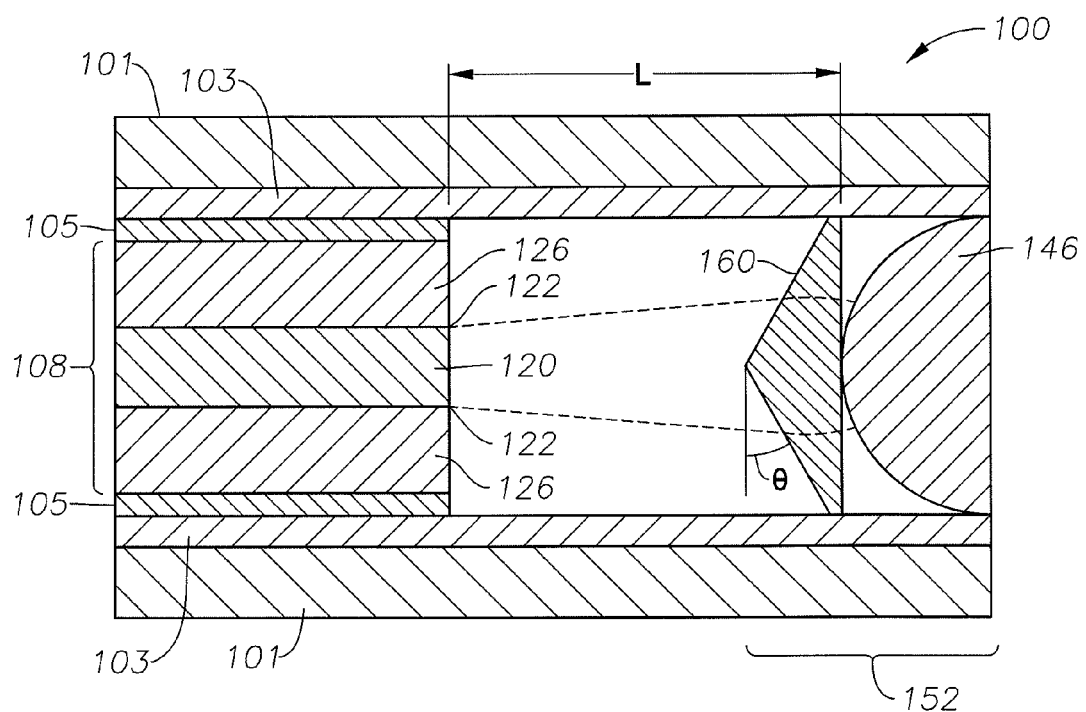
FIG. 5 illustrates an example of a multi-spot generator with a faceted optical element according to certain embodiments.

FIG. 5 illustrates an example of a multi-spot generator 152 with a faceted optical element. The faceted optical element is an element that is formed separately from the ball lens, unlike an optical element formed from an optical adhesive directly on the ball lens. The faceted optical element can be any suitable shape or size. In the example, the faceted optical element is a pyramid optical element 160 with N sides, where N=3, 4, 5, . . . . The pyramid optical element can comprise glass or plastic.

Length L represents a distance between the distal end of fiber 108 and the distal end of optical element 160 or the proximal end of ball lens 146. Angle θ represents the angle between a facet of optical element 160 and plane that is perpendicular to an axis of optical element 160. Length L and angle θ may have any suitable values. For example, if ball lens 146 is a 280 micron diameter sapphire ball, then length L may be between 190 and 310 microns and angle θ may be between 20 to 35 degrees.

Figures 6A, 6B, 6C:
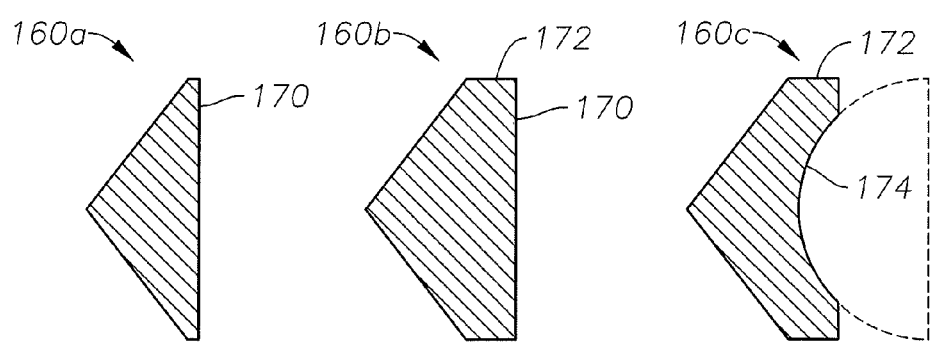
FIGS. 6A through 6C illustrate examples of pyramid optical elements according to certain embodiments.

FIGS. 6A through 6C illustrate examples of pyramid optical elements 160 (160a-b). A pyramid optical element 160 may be slip fit into short cannula 103 to ensure its proper clocking orientation relative to optical fiber 108.

Pyramid optical element 160a has a planar base surface 170. Pyramid optical element 160b has a thicker base 172, which may provide stability within short cannula 103. Thicker base 172 causes the optical axis to increase, which may modify the emitted beam spots. Pyramid optical element 160c has a concave base surface 174 with a concave portion within which a portion of a ball lens may be disposed. Concave base surface 174 may reduce the increase in the optical axis caused by thicker base 172.

Figure 7:
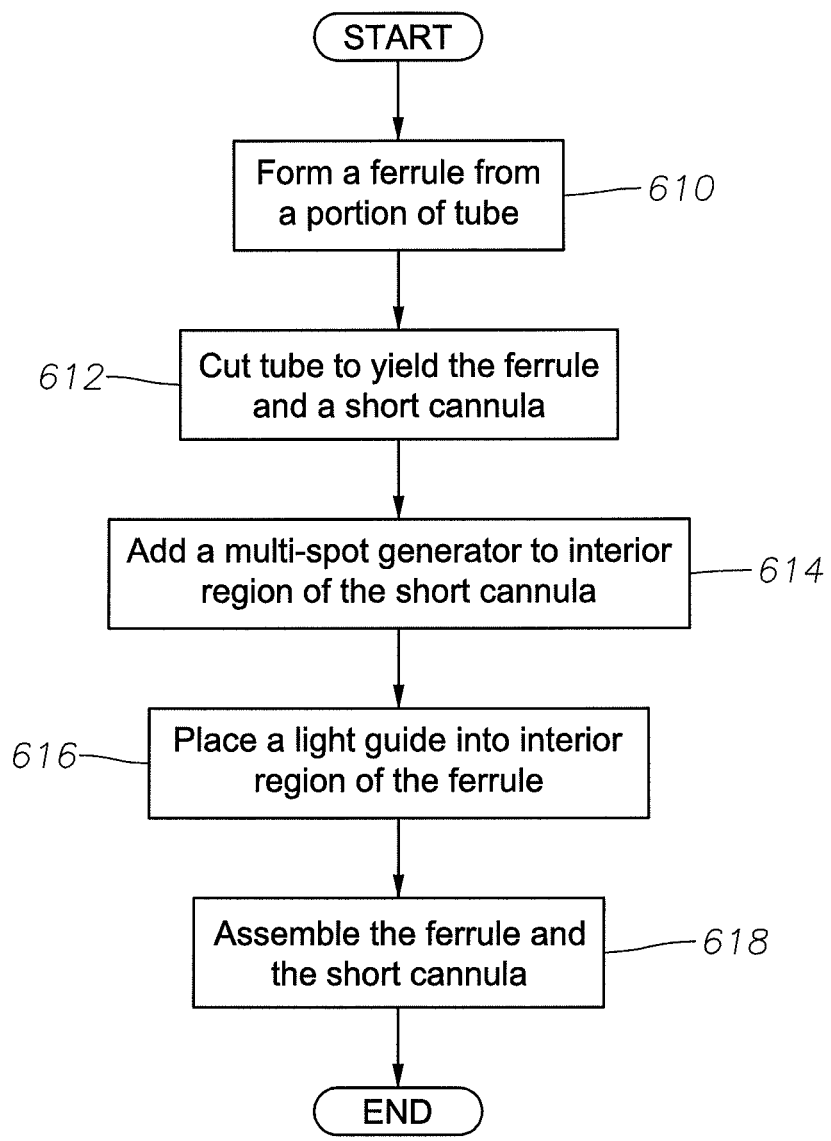
FIG. 7 illustrates an example of a method for manufacturing a laser probe long cannula according to certain embodiments.

FIG. 7 illustrates an example of a method for manufacturing a laser probe cannula. In the example, a short cannula and ferrule are fashioned from the same tube. The tube has an interior region. A first portion of the tube is used to form the ferrule, and a second portion of the tube is used to form the short cannula. The inner diameter of the tube may be selected according to the desired inner diameter of the resulting short cannula. For example, if the desired inner diameter is x microns, then a tube with an x micron inner diameter may be selected. The length of the tube may be the sum of the lengths of the ferrule and short cannula. The tube may comprise any suitable material, such as a metal, e.g., stainless steel.

The method starts at step 610, where a ferrule is formed from a portion of a tube. In certain embodiments, the portion is stamped into the shape and size of the ferrule. The ferrule may be substantially rotationally symmetric, e.g., cylindrically symmetric, such that when the ferrule is joined to the short cannula (at step 618), rotation of the ferrule with respect to the short cannula does not make a physical difference. The tube is cut at step 612 to yield the ferrule and the short cannula. In certain embodiments, the tube may be cut using a process that does not leave burrs, such as electric discharge machining (EDM). The tube may be cut at any suitable step of the method, such as before or after ferrule and/or short cannula is formed.

A multi-spot generator is added to the interior region of the short cannula at step 614. The multi-spot generator may be added in any suitable manner. In certain embodiments, a ball lens (which may be spherical or hemispherical) is inserted into the interior region of the short cannula. For example, the ball lens may be press-fit into the interior region such that the ball lens and short cannula are aligned. An optical adhesive is deposited into the distal end of the short cannula. For example, the optical adhesive may be placed onto a mold plate, and then the mold plate is inserted into the proximal end until it reaches the ball lens. The mold plate has the complementary shape of the desired faceted end surface and may have a molding pin and cannula guide to facilitate alignment with the cannula. The mold plate may push against the ball lens to center the lens. The optical adhesive is then cured to set the faceted end surface and the ball lens. For example, the optical adhesive may be cured with UV light. The molding plate may then be removed.

In certain embodiments, the ball lens is inserted into the interior region of the short cannula as above. A faceted optical element is placed in a proximal direction from the ball lens. The faceted optical element is placed to be aligned with the ball lens.

At least one optical fiber is placed into the interior region of the ferrule at step 616. In certain embodiments, an optical fiber is press-fit into the interior region of the ferrule. The ferrule may be shaped such that when the optical fiber is press-fit into the ferrule, the fiber is automatically aligned with the ferrule. The inner diameter of the ferrule may have one or more tapered regions to allow the fiber to easily fit into the ferrule.

The ferrule and the short cannula are assembled at step 618. In certain embodiments, the ferrule and short cannula are press-fit together. The ferrule and short cannula may be shaped such that, when they are press-fit together, they are automatically aligned. The outer diameter of the ferrule may have one or more tapered regions to allow the ferrule to easily fit into the short cannula.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A method comprising:
   forming a ferrule from a portion of a tube, the tube having an interior region;
   cutting the tube to yield the ferrule and a short cannula;
   adding a multi-spot generator to the interior region of the short cannula, the multi-spot generator having a faceted optical element with a faceted end surface, the adding the multi-spot generator further comprising:
      inserting a ball lens into the interior region of the short cannula, the diameter of the ball lens substantially equivalent to the diameter of the short cannula;
      depositing an optical adhesive in a proximal direction from the ball lens; and
      forming the faceted surface on the optical adhesive;
   placing at least one optical fiber into the interior region of the ferrule; and
   assembling the ferrule and the short cannula.

2. The method of claim 1, the depositing the optical adhesive further comprising:
   depositing an optical adhesive onto the ball lens using a mold plate.

3. The method of claim 1, the forming the faceted surface on the optical adhesive further comprising:
   curing the optical adhesive.

4. The method of claim 1, the adding the multi-spot generator further comprising:
   inserting a ball lens into the interior region of the short cannula; and
   inserting the faceted optical element in a proximal direction from the ball lens.

5. The method of claim 1, the forming the ferrule further comprising:
   stamping the portion into the shape and size of the ferrule.

6. The method of claim 1, the forming the ferrule further comprising:
   stamping the portion into a rotationally symmetric ferrule.

7. The method of claim 1, the placing at least one optical fiber into the interior region of the ferrule further comprising:
   press-fitting an optical fiber into the interior region of the ferrule.

8. The method of claim 1, the assembling the ferrule and the short cannula further comprising:
   press-fitting the ferrule and the short cannula.

9. A system comprising:
   a long cannula;
   at least one optical fiber disposed within the long cannula, the at least one optical fiber configured to carry a laser beam from a laser source to a distal end of the long cannula; and
   a multi-spot generator located at the distal end of the long cannula, the multi-spot generator comprising:
      a faceted optical element with a faceted end surface, the faceted end surface including at least one facet oblique to a path of the laser beam, the faceted optical element configured to receive the laser beam from the optical fiber; and
      a ball lens configured to receive the laser beam from the faceted optical element, the diameter of the ball lens substantially equivalent to the diameter of the long cannula, the faceted optical element formed separately from the ball lens.

10. The system of claim 9, the faceted optical element comprising a pyramid optical element.

11. The system of claim 9, the faceted optical element comprising a pyramid optical element with a planar base surface.

12. The system of claim 9, the faceted optical element comprising a pyramid optical element having a base surface with a concave portion within which at least a portion of the ball lens is disposed.

13. A system comprising:
   a long cannula;
   at least one optical fiber disposed within the long cannula, the at least one optical fiber configured to carry a laser beam from a laser source to a distal end of the long cannula; and
   a multi-spot generator located at the distal end of the long cannula, the multi-spot generator comprising:
      a faceted optical element with a faceted end surface, the faceted end surface including at least one facet oblique to a path of the laser beam, the faceted optical element configured to receive the laser beam from the optical fiber; and
      a hemispherical ball lens configured to receive the laser beam from the faceted optical element, the hemispherical ball lens having a planar surface that is substantially flush with a distal end of the long cannula.

14. The system of claim 13, the faceted optical element comprising an optical adhesive deposited onto the hemispherical ball lens.

15. The system of claim 13, the faceted optical element comprising an optical element formed separately from the hemispherical ball lens.

16. The system of claim 13, the faceted optical element comprising a pyramid optical element.

* * * * *